United States Patent [19]
Budgifvars et al.

[11] Patent Number: 6,029,088
[45] Date of Patent: Feb. 22, 2000

[54] HEART STIMULATOR WITH AN EVOKED RESPONSE DETECTOR

[75] Inventors: Goran Budgifvars, Spanga; Asa Uhrenius; Peter Andersson, both of Stockholm, all of Sweden

[73] Assignee: Pacesetter AB, Järfälla, Sweden

[21] Appl. No.: 09/161,665

[22] Filed: Sep. 29, 1998

[30] Foreign Application Priority Data

Oct. 2, 1997 [SE] Sweden ................................ 9703600

[51] Int. Cl.[7] .................................................. A61N 1/18
[52] U.S. Cl. ............................................................ 607/27
[58] Field of Search ........................................ 607/27, 28

[56] References Cited

U.S. PATENT DOCUMENTS

| | | | |
|---|---|---|---|
| 4,537,201 | 8/1985 | Delle-Vedove et al. | 607/27 |
| 4,858,610 | 8/1989 | Callaghan et al. | 607/28 |
| 5,265,601 | 11/1993 | Mehra . | |
| 5,350,410 | 9/1994 | Kleks et al. . | |
| 5,417,718 | 5/1995 | Kleks et al. . | |
| 5,431,693 | 7/1995 | Schroeppel . | |
| 5,447,525 | 9/1995 | Powell et al. | 607/28 |
| 5,458,623 | 10/1995 | Lu et al. . | |
| 5,476,486 | 12/1995 | Lu et al. | 607/28 |

FOREIGN PATENT DOCUMENTS

| | | |
|---|---|---|
| 0 372 698 | 6/1990 | European Pat. Off. . |
| WO 95/07114 | 3/1995 | WIPO . |

*Primary Examiner*—William E. Kamm
*Attorney, Agent, or Firm*—Hill & Simpson

[57] ABSTRACT

An evoked response detector for a heart stimulator determines evoked response in the presence of polarization. The heart stimulator has a pulse generator which produces stimulation pulses of varying amplitudes, and a lead adapted for introduction into the heart of a patient is connected to the pulse generator for delivering stimulation pulses to the heart. The evoked response detector includes measuring and memory circuitry for measuring and storing the electrode signals picked up by the lead in response to the delivered stimulation pulses, at least one of these stimulation pulses having a sufficiently high amplitude for obtaining capture. Each measured electrode signal contains two signal components, one of these signal components being proportional to the amplitude of the associated stimulation pulse and the other signal component being substantially constant, independent of the associated stimulation pulse amplitude. An analyzing unit determines the evoked response signal from a predetermined relation between the amplitudes of at least two stimulation pulses of different amplitudes and the resulting measured electrode signals.

18 Claims, 3 Drawing Sheets

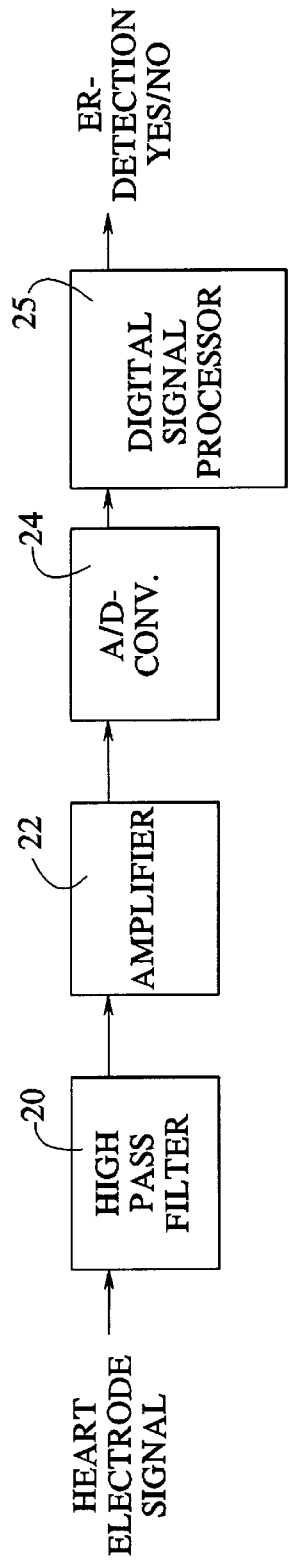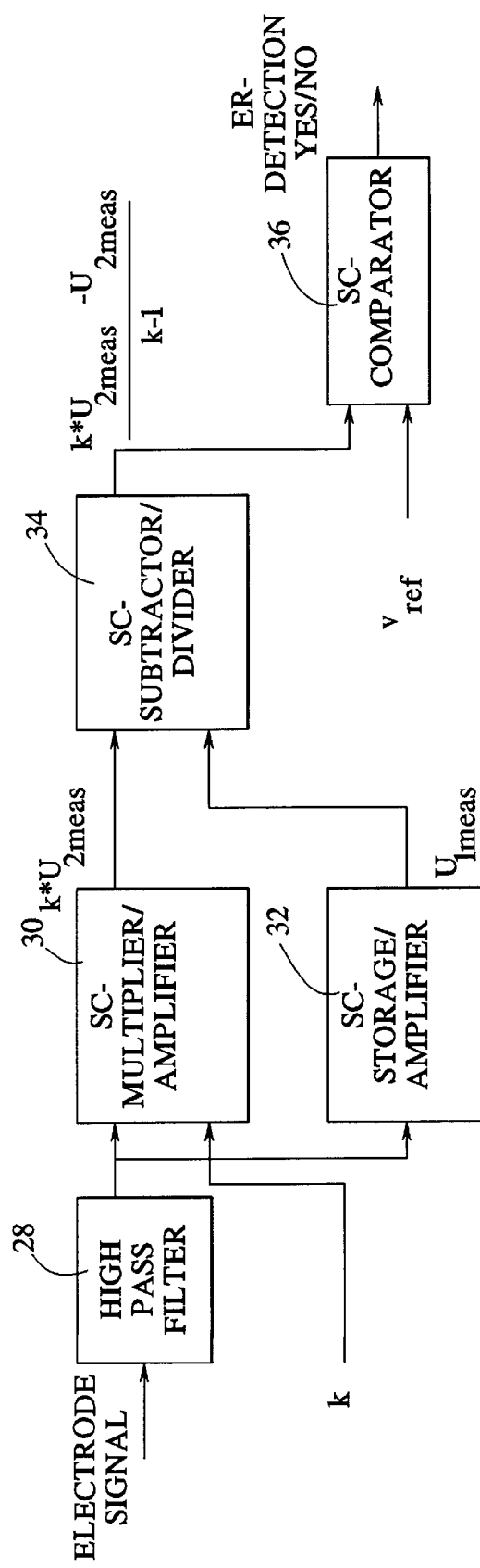

HEART STIMULATOR WITH AN EVOKED RESPONSE DETECTOR

BACKGROUND OF THE INVENTION

1. Field of the Invention

The present invention relates to an evoked response detector for a heart stimulator for determining evoked response in the presence of polarization, and to a heart stimulator having such an evoked response detector incorporated therein.

2. Description of the Prior Art

Cardiac stimulators are known which have a pulse generator devised for producing stimulation pulses of varying amplitudes, and a lead adopted to be introduced into the heart of a patient and connected to the pulse generator for delivering stimulation pulses to the heart, and an evoked response detector having measuring and memory means for measuring and storing the electrode signal picked up by the lead in response to delivered stimulation pulses, wherein at least one of said stimulation pulses has a sufficiently high amplitude for obtaining capture.

To reduce the energy consumption of heart stimulators a so called AUTOCAPTURE™ function is used to maintain the energy of the stimulation pulses at a level just above that which is needed to effectuate capture, cf. e.g. U.S. Pat. No. 5,458,623. A reliable detection of the evoked response, which then is necessary, is, however, not a simple matter, especially when it is desired to sense the evoked response with the same electrode as the one delivering the stimulation pulse. This is because of the fact that the evoked response potential could be small in amplitude compared to the residual polarization charge. The residual charge decays exponentially but tends to dominate the evoked potential for several hundreds of milliseconds after the stimulation. If the polarization is too high, it could be wrongly interpreted by the evoked response detector as a capture, i.e. contraction of the heart. The AUTOCAPTURE™ algorithm could then by mistake adjust the output amplitude of the stimulation pulse to a value below the actual capture level, which will result in no capture. If the electrode surface of the electrode lead in use has significant polarization this could consequently disturb the AUTOCAPTURE™ function and result in loss of capture. To guarantee a safe and reliable detection of evoked response it is thus desirable to use leads having electrode surfaces with low polarization.

Several attempts have been made to solve the lead polarization problems in connection with evoked response detection. Thus U.S. Pat. No. 5,417,718 discloses a system for maintaining capture wherein electrical post-stimulus signal of the heart, following delivery of a stimulation pulse, is compared to a polarization template, determined during a capture verification test. A prescribed difference between the polarization template and the post-stimulus signal indicates capture. Otherwise loss of capture is presumed and the stimulation energy is increased a predetermined amount to obtain capture.

There is mostly at least one significant slope in the bipolar measured IEGM signal, which makes it possible to discriminate the evoked response signal from slowly varying signals such as polarization signals. Thus in U.S. Pat. No. 5,431,693 a method of verifying capture of the heart by a cardiac pacemaker is described by observing that the non-capture potential is exponential in form and the evoked capture potential, while generally exponential in form, has one or more small-amplitude perturbations superimposed on the exponential wave form. These perturbations are enhanced for ease of detection by processing the wave form signal by differentiation to form the second derivative of the evoked response signal for analysis for the evoked response detection.

Unipolar detection of evoked response signals is, however, not possible using this technique. Abrupt slope changes or superimposed small-amplitude perturbations are leveled out if the measurements are made over a longer distance from the electrode to the stimulator casing.

Experiments have now shown that the evoked response signal amplitude is fairly constant, independent of the stimulation pulse amplitude, i.e. the evoked response signal amplitude does not vary with the amplitude of the stimulation pulse (provided that the stimulation amplitude is above the capture threshold) Further, it has been found that the electrode polarization is approximately linearly dependent on the stimulation pulse amplitude for a constant pulse duration. Experimental results are presented in greater detail below in connection with the description of FIGS. 1–3.

SUMMARY OF THE INVENTION

An object of the present invention is to provide an improved detector for determining evoked response based on the above discoveries, which can be used not only in a bipolar mode of operation but also in a unipolar mode.

The above object is achieved in accordance with the principles of the present invention in a heart stimulator having a pulse generator which supplies stimulation pulses, via an implanted lead, to cardiac tissue of a subject, the lead picking up successive electrode signals respectively produced by the cardiac tissue in response to the stimulation pulses, the electrode signals each having a signal component which is substantially proportional to the amplitude of the associated stimulation pulse and an evoked response component which is independent of the amplitude of the associated stimulation pulse, and an evoked response detector including measuring and memory means for measuring and storing respective amplitudes of the electrode signals, and an analysis unit supplied with respective amplitudes of two stimulation pulses and respective measured amplitudes of two associated electrode signals, for determining an evoked response signal from a predetermined relation among these amplitudes. One of the amplitudes of the stimulation pulses is sufficiently high to obtain safe capture, and the other supplied amplitude of a stimulation pulse is less than the amplitude which produced safe capture.

The detector according to the invention can be used also for unipolar detection of evoked response, which is an important advantage since unipolar leads are less complicated to manufacture and have longer working life than bipolar electrodes. In addition there is a desire to extend the use of heart stimulators, like pacemakers with AUTOCAPTURE™ function, to patients with chronic unipolar leads. Another advantage of the detector according to the invention is that no extra stimulation pulse, resulting in extended current drain, is needed for measuring the polarization as in known techniques, where stimulations and measurement of polarization are performed in the refractory period of the heart. Further, no extra test is required for tuning the sensitivity of the evoked response detector, contrary to the situation in prior art pacemakers, in which separate tests are used to find evoked response, polarization and capture threshold levels.

Thus, with the detector according to the invention, the cardiac signal is measured and stored at two different stimulation voltages, at least one of these voltages being sufficient for producing capture. From these stimulation voltages and the resulting measured electrode signals, polarization signal level, evoked response signal level and capture threshold level can be calculated as will be described more in detail below. As mentioned above an important advantage compared to prior art methods is that no stimulation is required in the refractory period of the heart for determining the electrode polarization level.

In an embodiment of the device according to the invention, the evoked response detector includes an averaging unit for forming an average value of electrode signals picked up by the electrode lead in an evoked response window in response to each stimulation pulse of a number of delivered stimulation pulses of constant amplitude. In this way small variations in the measured evoked response and polarization signals are suppressed.

In another embodiment of the detector according to the invention, the evoked response detector includes a timers for automatically initiating a check at regular time intervals and, when necessary, triggering adjustment of the sensitivity threshold of the detector. The threshold sensitivity is defined as $Pol_x + ER = U_{xmeas}$, where $Pol_x$ and $U_{xmeas}$ designate the polarization and the measured electrode signal respectively resulting from the stimulation pulse having the amplitude $U_{xstim}$. In this way it is possible to automatically adapt the evoked response sensitivity threshold to changes in the polarization and the evoked response signal without the pacemaker programmer being present.

In another embodiment of the detector according to the invention an integrating unit is provided for integrating the picked up electrode signal within a programmable portion of the evoked response window. Electromagnetic interference and other periodic interference signals are then suppressed.

In accordance with the invention a heart stimulator includes a device for determining capture stimulation level, as described above preferably for realizing an AUTOCAPTURE™ function.

DESCRIPTION OF THE DRAWINGS

FIG. 6 is a block diagram of another embodiment of the evoked response detector according to the invention.

FIG. 7 is a block diagram of the evoked response detector according to the invention implemented in switched capacitor technique.

DESCRIPTION OF THE PREFERRED EMBODIMENTS

Figure 1:
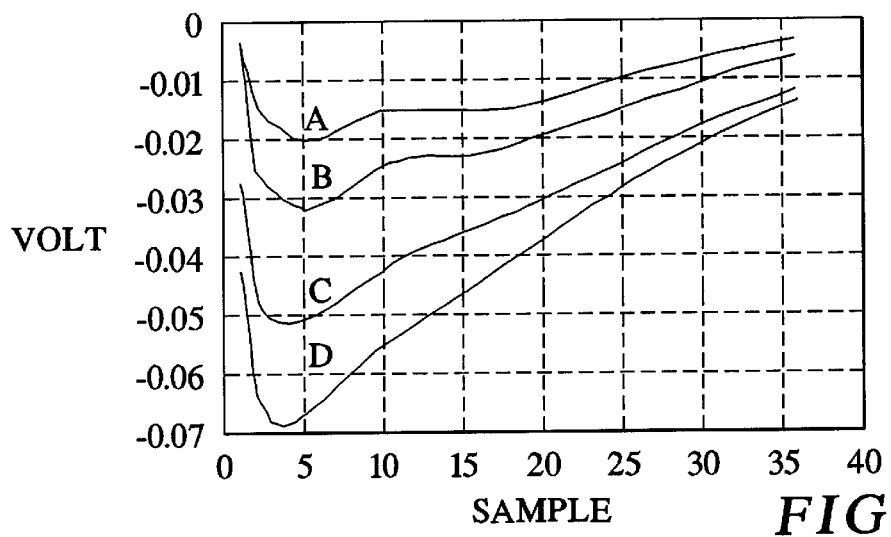
FIG. 1 shows the electrode signal (IEGM) for four different stimulation pulse amplitudes as a function of time from immediately after the stimulation complex is delivered, sample 0, to approximately 80 msec after the stimulation complex, sample 40.

The polarization of the pacemaker electrode can be described as $$Pol = \frac{U_{stim}}{\alpha} * f(dur, RC_{output}) \quad (1)$$

where Pol designates the polarization signal, $U_{stim}$ the pacemaker stimulation pulse amplitude, $\alpha$ is a constant, dur designates the duration of the stimulation pulse and $RC_{output}$ is the time constant of the pacemaker output lead system (see Konrad Mund, "Analysis of the polarization and the sensing behavior of electrodes for cardiac pacemakers", Pacemaker leads, pp. 503–509, Elsevier Science Publishers By, 1991).

Thus, according to equation (1) above the polarization is a function of the duration dur of the stimulation pulse and the time constant $RC_{output}$. This means that if the duration dur of the stimulation pulse and the time constant $RC_{output}$ are constant for different stimulation pulse amplitudes the polarization Pol is only dependent on the stimulation pulse amplitude $U_{stim}$ and this dependency is linear.

Studies on animals show that the evoked response signal amplitude ER is fairly constant for different stimulation pulse amplitudes $U_{stim}$ and independent of the stimulation pulse duration dur. Accordingly the following relations are valid.

$$Pol_1 + ER = U_{1meas} \quad (2)$$

$$Pol_2 = \frac{Pol_1}{k} \quad (3)$$

$$Pol_2 + ER = U_{2meas} \quad (4)$$

where $$k = \frac{U_{1stim}}{U_{2stim}} \quad (5)$$

$U_{1stim}$ designates a stimulation pulse amplitude which is supposed to be higher than $U_{2stim}$ and high enough for producing capture. $U_{1meas}$ designates the measured electrode signal consisting of the measured evoked response signal amplitude ER+possible polarization signal $Pol_1$ for the stimulation pulse amplitude $U_{1stim}$ and $U_{2meas}$ is the measured evoked response signal amplitude ER+possible polarization signal $Pol_2$ for the stimulation pulse amplitude $U_{2stim}$.

From the equations above the evoked response signal amplitude ER can be determined as $$ER = \frac{(k * U_{2meas}) - U_{1meas}}{k - 1} \quad (6)$$

where $$k = \frac{U_{1stim}}{U_{2stim}} \quad (7)$$

The loss of capture level is given by the relation $$U_{2meas} = \frac{U_{1meas} - ER}{k} \quad (8)$$

which is obtained by putting ER equal to zero in equation (4) above, i.e. $Pol_2 = U_{2meas}$, if $U_{2stim}$ results in loss of capture.

The capture threshold level is then equal to the one step higher stimulation pulse amplitude.

In practice the capture threshold level is determined as follows. To start, stimulation is performed with a pulse amplitude that gives the highest available probability for capture, preferably with the highest output pulse amplitude (typically 4.5V). The electrode signal which consists of the evoked response signal and polarization signal, is measured during a predetermined evoked response window after stimulation and the signal is stored. These steps are preferably repeated one to five times at the programmed stimulation pulse amplitude and an average of the measured electrode signals is calculated in order to suppress small variations in the measured evoked response and polarization signals.

After this formation of an average value, the procedure above is repeated for successively decreasing stimulation pulse amplitudes until the loss of capture stimulation amplitude is found, given by equation (8) above.

The evoked response signal is calculated from equation (6) above. The most reliable result is obtained by using measured electrode signals for the highest stimulation pulse amplitude and a lower one. Also measured electrode signals for lower stimulation pulse amplitudes can be used as long as the stimulation pulse amplitudes are above the stimulation threshold.

The polarization signal can then be calculated for a certain stimulation pulse amplitude from equations (2) and (3). The polarization signal can be calculated for stimulation pulse amplitudes both above and below the stimulation threshold, for stimulation pulse amplitudes below the stimulation thresholds the evoked response signal being equal to zero.

If one polarization signal $Pol_1$ is known it is then possible to calculate the polarization signal $Pol_2$, for a following specific pulse amplitude by using the equations (3) and (5).

By using the equations above it is also possible to determine the evoked response detector sensitivity. This could be done in two ways, one of which is according to the relation $$\text{sensitivity threshold} = Pol_x + ER = U_{xmeas}$$

where x indicates the order of the present stimulation. This means that a unique sensitivity has to be programmed for each stimulation pulse amplitude if polarization is present.

The other possibility of determining the detector sensibility is to subtract the calculated polarization signals for the actual stimulation pulse amplitude from the measured electrode signal. This will give the evoked response signal level which is equal to the sensitivity threshold.

Each of the above described alternatives for determining the detector sensitivity requires stored values of the calculated evoked response signal and the calculated polarization signal to correctly calculate the sensitivity threshold for each stimulation pulse amplitude.

Since the algorithm of the detector according to the invention can be integrated into the threshold search algorithm, no extra test is required for tuning the sensitivity of the evoked response detector, contrary to what is needed in prior art pacemakers, in which separate tests are used to find evoked response, polarization and threshold levels.

FIG. 1 shows the electrode signal (IEGM) for different stimulation amplitudes as a function of time. Thus the electrode signals are recorded from a time immediately after the stimulation complex is delivered, sample 0, until approximately 80 msec after the stimulation, sample 40. Curve A is obtained for a stimulation pulse amplitude of 0.6 V, curve B is obtained for a stimulation pulse amplitude of 1.5 V, curve C is obtained for a stimulation pulse amplitude of 3.0 V, and curve D for a stimulation pulse amplitude of 4.5 V. All curves A–D are averaged from five measurements.

Each curve represents the sum of the evoked response signal and the polarization signal. Since the evoked response signal is essentially constant it is apparent from FIG. 1 that the polarization signal varies significantly with the used stimulation pulse amplitude, the shown maximum variation amounting to approximately 50 mV.

Figure 2:
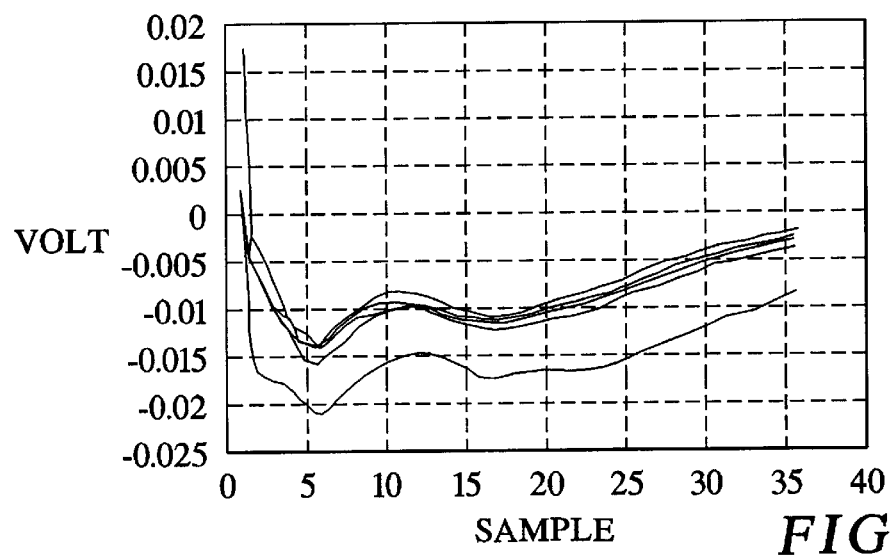
FIG. 2 shows the "real" or "clean" evoked response signal as a function of time calculated from the measured signals in FIG. 1.

With the aid of equation (6) above, the "real" or "clean" evoked response signals, without polarization signal can be calculated from the data in FIG. 1, and in FIG. 2 these calculated evoked response signals are shown as a function of time for all possible stimulation amplitude combinations, namely $$k = \frac{U_{1stim}}{U_{2stim}}$$

=4.5/3, 4.5/1.5, 4.5/0.6, 3.0/1.5, 3.0/0.6, and 1.5/0.6. The lowest curve in FIG. 2 is obtained for K=4.5/3 and this curve is shifted away from the others for some reason not fully investigated.

Figure 3:
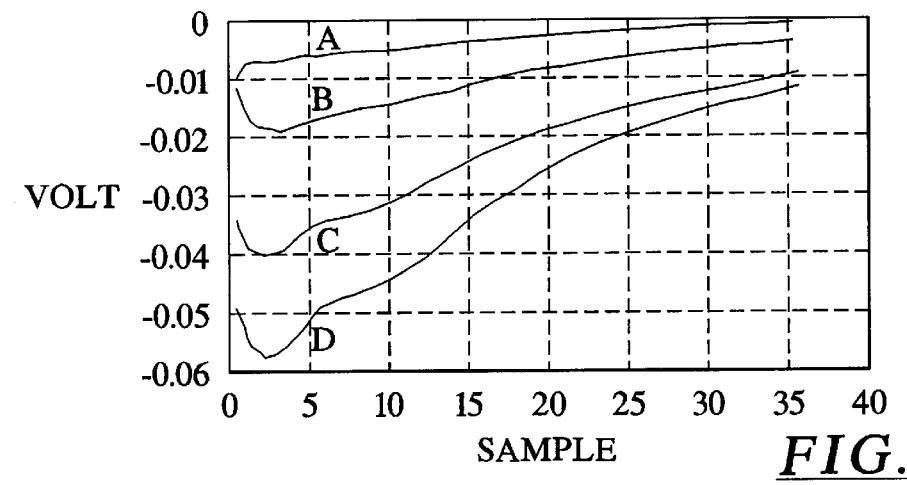
FIG. 3 shows the polarization signals as a function of time calculated from the measured electrode signals in FIG. 1.

In FIG. 3 the polarization signals for corresponding stimulation pulse amplitudes are shown. These polarization signals are calculated by the relation $$Pol = U_{xmeas} - ER_{ave}$$

where $ER_{ave}$ denotes the average curve of the calculated "real" evoked response signals shown in FIG. 2. The curves marked by A, B, C and D correspond to the curves A, B, C, D respectively in FIG. 1.

Figure 4:
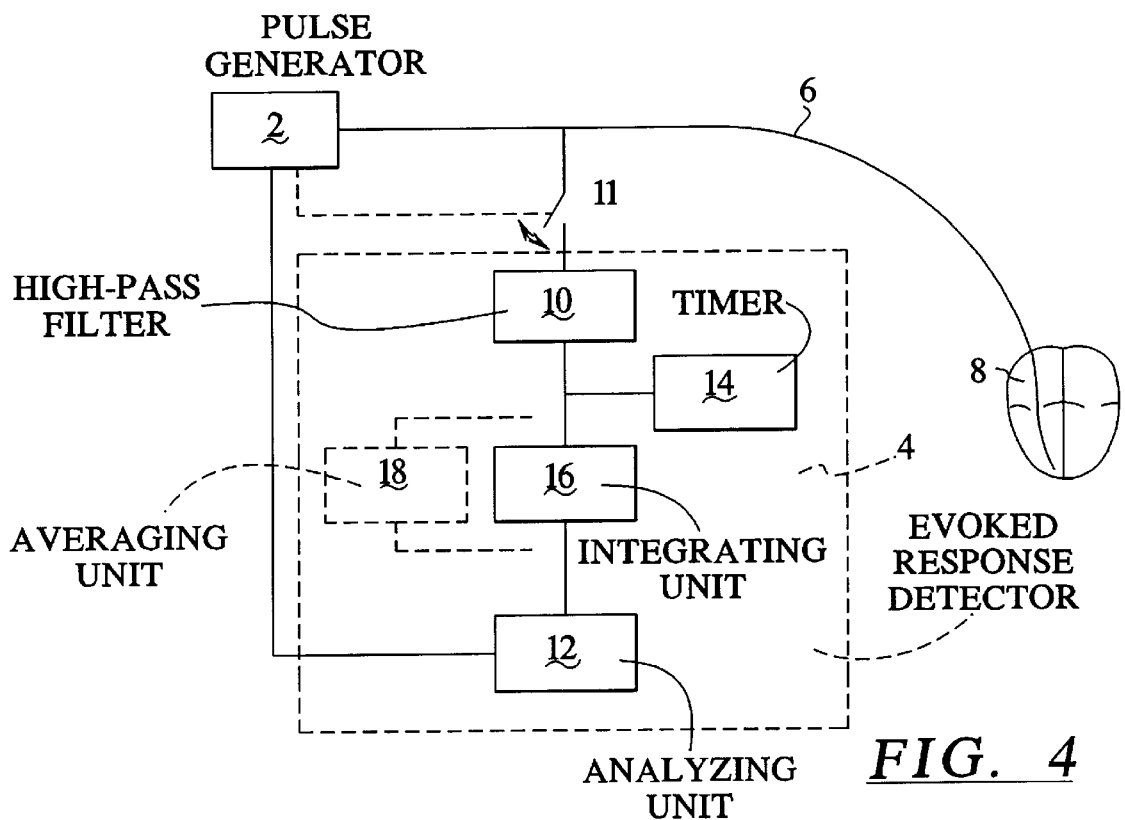
FIG. 4 is a block diagram of the basic components of the detector according to the invention.

FIG. 4 shows a block diagram of the basic components of the detector according to the invention incorporated in a heart stimulator. The stimulator has a pulse generator 2 which is connected to the heart 8 of a patient via a lead 6. The pulse generator 2 is devised to produce stimulation pulses of varying amplitudes which through the lead 6 are delivered to the heart 8. The evoked response detector 4 is also connected to the lead 6. The evoked response detector 4 contains a high-pass filter 10 for eliminating the DC level in the electrode signal picked up by the lead 6. The filter cut-off frequency should be low enough so as not to distort the low frequency content of the electrode signal, preferably 1 Hz or lower.

The high-pass filtered electrode signal is supplied to an integrating unit 16 (see below) and to an analyzing unit 12 for determining the capture stimulation level from a predetermined relation between the amplitudes of at least two stimulation pulses of different amplitudes and the resulting measured electrode signals, as described above.

The high-pass filter 10 is disconnected from the lead 6 during stimulation by a switch 11. As a consequence the electrode signal obtained before the stimulation in question will be stored in the filter 10. When the evoked response detector is enabled after a stimulation, the difference between the electrode signal before stimulation and after is supplied to the analyzing unit 12.

A timer 14 determines an ER-window during which the electrode signal is measured and stored. This ER-window normally extends from 0 to 62.5 msec after stimulation.

To suppress electromagnetic interference and other periodic interference signals an integrating unit 16 can be provided to integrate the electrode signal from the beginning of the evoked response or ER-window to normally 40 msec. The exact duration of the integration time and the start of the integration in the ER-window is programmable.

As an alternative an averaging unit 18 can be provided for forming the average value of a predetermined number of measured electrode signals.

When the detector according to the invention is implemented in a pacemaker special measures have to be taken for obtaining correct measurements when activating the evoked response detector in the ER-window.

Figure 5:
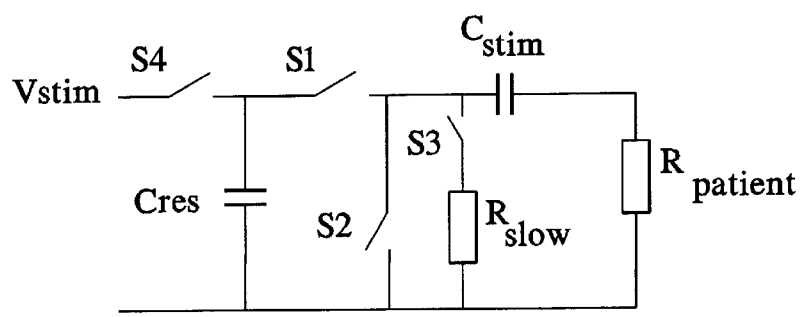
FIG. 5 is a circuit diagram of the output stage of a pacemaker into which a detector according to the invention can be implemented.

FIG. 5 is a circuit diagram of the output stage of a pacemaker. In this output stage the output capacitor $C_{stim}$ is always empty before stimulation, otherwise the output amplitude will be undesirably low. Before stimulation, capacitor $C_{res}$ is charged to the desired stimulation voltage, $V_{stim}$. When a stimulation pulse is generated the following occurs:

The switches S2, S3, and S4 are opened. The switch S1 is closed and the capacitor $C_{stim}$ is thereby charged by capacitor $C_{res}$. A current is now flowing through the patient load represented by the resistor $R_{patient}$ and the resulting voltage drop generates a stimulation pulse. After approximately 1 msec the stimulation is terminated and the switch S1 is opened and the switch S2 is closed, which results in a fast discharge of the capacitor $C_{stim}$. After about 6 msec the fast discharge is terminated and the switch S2 is opened. The switch S3 is then closed and in this way a slowly discharging resistor $R_{slow}$ of about 25 kohm is connected. After another 6 msec the evoked response detector is activated. If the fast discharge were not performed, a considerably higher current would have passed through the resistor $R_{patient}$ when connecting the resistor $R_{slow}$, which would result in disturbances during the evoked response detection. Thus the slowly discharging resistor $R_{slow}$ in the pacemaker output stage should not be connected during the ER-window as it could disturb the electrode signal.

FIG. 6 shows in more detail one embodiment of the evoked response detector according to the invention. The heart electrode signal picked up by the lead 6 in FIG. 4 is then supplied to a high-pass filter 20. An amplifier 22 and an A/D converter 24 are provided for amplifying and A/D converting respectively the filtered signal. A digital signal processor 26 calculates the evoked response signal according to equation (6) above and compares the calculated ER-value with a predetermined reference value to determine whether evoked response is detected.

Thus in the embodiment shown in FIG. 6 the algorithm for determining whether an evoked response is detected or not is implemented in software by use of a microprocessor. Instead of using a microprocessor this algorithm can be implemented in random logic, which means realization by ordinary logic elements, that is logic gates.

The detector according to the invention can also be implemented in the pacemaker electronics by use of switched capacitor (SC) technique. The algorithm is then implemented in SC technique, where different capacitors serve as memory elements for storing the different electrode potentials and SC-adding, subtracting and multiplying circuits are used for performing the necessary calculations as explained above.

FIG. 7 shows a block diagram of an embodiment of the evoked response detector according to the invention implemented in such switched capacitor technique. The heart electrode signal, picked up by the lead 6 in FIG. 4, is supplied to a high-pass filter 28. The filtered signal resulting from a stimulation with a pulse amplitude of $U_{1stim}$ is supplied to a SC storage/amplifier 32 and the resulting output signal $U_{1meas}$ is delivered to a SC subtractor 34.

The filtered electrode signal resulting from stimulation with the pulse amplitude $U_2$stim is supplied to a SC multiplier/amplifier 30 together with the constant k according to equation (5) above, and the output signal $k*U_{2meas}$ is delivered to the SC subtractor 34, too. In the subtractor/divider 34 $ER=(k*U_{2meas}-U_{1meas})/k-1$ is formed and supplied to a SC comparator 36 and compared with a reference voltage $V_{ref}$ for determining whether an evoked response is detected or not. The signal "ER-detection yes/no" is then transferred to the logic unit of the pacemaker for controlling the pacemaker.

When implementing the detector according to the invention in pacemaker electronics, this can be done by modifying the automatic threshold search algorithm that is normally used. The threshold search is normally done every eight hours and should then be modified to stimulate several times for every stimulation pulse amplitude to make it possible to take the average value over several measured evoked response and polarization signals. Automatic measurement of the evoked response signal every eight hours also makes it possible to automatically adapt the evoked response sensitivity threshold to changes in the polarization and evoked response signal without a pacemaker programmer present.

The detector according to the invention can, however, also be implemented into the pacemaker programmer to determine the evoked response signal level, polarization value and capture threshold level at implantation of the pacemaker.

The detector according to the invention can also be used for automatic adjustment of the output stage fast discharge time to minimize the electrode polarization voltage, cf. FIG. 5 above.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator comprising:

a pulse generator which emits stimulation pulses of various amplitudes, said stimulation pulses including one of said stimulation pulses having an amplitude $U_{1stim}$ which is sufficiently high for obtaining safe capture and another of said stimulation pulses having an amplitude $U_{2stim}$ which is less than $U_{1stim}$;

a lead connected to said pulse generator and adapted for implantation in a subject to deliver said stimulation pulses to cardiac tissue in said subject and to pick up successive electrode signals respective produced by cardiac tissue in response to said stimulation pulses, said electrode signals thus being respectively associated with said stimulation pulses, and each of said electrode signals comprising a signal component which is substantially proportional to the amplitude of the associated stimulation pulse and an evoked response component which is independent of the amplitude of the associated stimulation pulse;

measuring and memory means for measuring and storing a measured amplitude $U_{1meas}$ for the electrode signal associated with said one of said stimulation pulses having the amplitude $U_{1stim}$ and a measured amplitude $U_{2meas}$ for the electrode signal associated with the other of said stimulation pulses having the amplitude $U_{2stim}$; and analyzer means supplied with $U_{1stim}$, $U_{2stim}$, $U_{1meas}$ and $U_{2meas}$ for detecting an evoked response signal from a predetermined relation among $U_{1stim}$, $U_{2stim}$, $U_{1meas}$ and $U_{2meas}$.

2. A heart stimulator as claimed in claim 1 wherein said analyzer means comprises means for determining said evoked response signal from the predetermined relation $$ER = \frac{(k * U_{2meas}) - U_{1meas}}{k - 1}$$

wherein ER is a signal amplitude of said evoked response signal and wherein $k=U_{1stim}/U_{2stim}$.

3. A heart stimulator as claimed in claim 1 further comprising averaging means for forming an average value of said electrode signals picked up by said electrode lead within an evoked response window respectively following each stimulation pulse of a plurality of stimulation pulses of equal amplitudes.

4. A heart stimulator as claimed in claim 1 wherein said measuring and memory means measures and stores said successive electrode signals respectively picked up in an evoked response window of a predetermined length after each of said stimulation pulses.

5. A heart stimulator as claimed in claim 1 wherein said measuring and memory means has an evoked response window of 62.5 msec.

6. A heart stimulator as claimed in claim 1 wherein said pulse generator emits said stimulation pulses having successively decreasing amplitudes.

7. A heart stimulator as claimed in claim 1 further comprising an extracorporeal programmer, and wherein said analyzing means is disposed in said extracorporeal programmer.

8. A heart stimulator as claimed in claim 1 comprising a housing containing said pulse generator, said measuring and memory means and said analyzer means, said housing being adapted for implantation in said subject.

9. A heart stimulator as claimed in claim 8 further comprising timing means for automatically initiating, at regular time intervals, a check and, if necessary an adjustment, of a sensitivity threshold defined as $Pol_x + ER = U_{xmeas}$, wherein $Pol_x$ and $U_{xmeas}$ respectively designate the polarization and the measured electrode signal respectively resulting from a stimulation pulse having an amplitude $U_{xstim}$, and wherein ER is an amplitude of said evoked response signal.

10. A heart stimulator as claimed in claim 1 wherein said successive electrode signals have a low-frequency content, and wherein said heart stimulator further comprises a high-pass filter for filtering said electrode signals, said filter having a cut-off frequency which does not distort said low-frequency content of said electrode signals.

11. A heart stimulator as claimed in claim 10 further comprising means for disconnecting said high-pass filter from said electrode lead during emission of each of said stimulation pulses.

12. A heart stimulator as claimed in claim 1 further comprising integrating means for integrating said electrode signals within a programmable portion of an evoked response window.

13. A heart stimulator as claimed in claim 1 wherein said measuring and memory means and said analyzer means comprise circuits constructed using switched capacitor technique.

14. A heart stimulator as claimed in claim 1 wherein said measuring and memory means and said analyzer means comprise an amplifier, an analog-to-digital converter and a microprocessor.

15. A heart stimulator as claimed in claim 1 wherein said measuring and memory means and said analyzer means comprise an amplifier, an analog-to-digital converter and a random logic components.

16. A heart stimulator as claimed in claim 1 further comprising control means, supplied with said evoked response signal, for setting the respective amplitudes of said stimulation pulses dependent on said evoked response signal.

17. A heart stimulator as claimed in claim 1 wherein said lead comprises a bipolar lead.

18. A heart stimulator as claimed in claim 1 wherein said lead comprises a unipolar lead.

* * * * *